United States Patent [19]

Grollier et al.

[11] 4,170,452
[45] Oct. 9, 1979

[54] DYE COMPOSITION CONTAINING DIPHENYLAMINE AND POLYHYDROXYBENZENE

[75] Inventors: Jean-Francois Grollier, Paris; Christian Monnais, Neuilly-sur-Seine; Chantal Fourcadier, Paris, all of France

[73] Assignee: L'Oreal, Paris, France

[21] Appl. No.: 760,390

[22] Filed: Jan. 18, 1977

[30] Foreign Application Priority Data

Jan. 19, 1976 [FR] France .............................. 76 01252

[51] Int. Cl.$^2$ .............................................. A61K 7/13
[52] U.S. Cl. ........................................ 8/10.2; 8/10; 8/10.1; 8/11; 8/32
[58] Field of Search ............................. 8/10.2, 11, 32

[56] References Cited

U.S. PATENT DOCUMENTS

| | | | |
|---|---|---|---|
| 3,214,472 | 10/1965 | Charle et al. ................ | 8/10.2 X |
| 3,251,742 | 5/1966 | Soloway .................... | 8/10.2 |
| 3,488,138 | 1/1970 | Iscowitz ................... | 8/10.2 X |
| 3,787,174 | 1/1974 | Kalopissis et al. ............ | 8/11 |
| 3,792,090 | 2/1974 | Kalopissis et al. ............ | 8/10.2 X |
| 3,853,464 | 12/1974 | Kalopissis et al. ............ | 8/10.2 X |
| 3,884,627 | 5/1975 | Brody et al. ................ | 8/10.2 |
| 3,905,761 | 9/1975 | Kalopissis et al. ............ | 8/10.2 |
| 3,920,384 | 11/1975 | Feinland et al. .............. | 8/10.2 |
| 3,977,826 | 8/1976 | Iscowitz ................... | 8/10.2 |
| 4,008,043 | 2/1977 | Kalopissis et al. ............ | 8/10.2 |

FOREIGN PATENT DOCUMENTS

| | | | |
|---|---|---|---|
| 710134 | 6/1954 | United Kingdom ............ | 8/10.2 |
| 745532 | 2/1956 | United Kingdom ............ | 8/10.2 |

Primary Examiner—James O. Thomas, Jr.
Assistant Examiner—Vera C. Clarke
Attorney, Agent, or Firm—Cushman, Darby & Cushman

[57] ABSTRACT

A dye composition for keratinic fiber and particularly living human hair comprises an admixture of one or more diphenylamines whose corresponding indoamine has an oxidation-reduction potential between −450 and −350 mv and a polyhydroxybenzene having an oxidation-reduction potential between −600 and −300 mv and having the formula

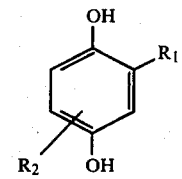

wherein $R_1$ represents hydroxy or

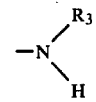

wherein $R_3$ represents hydrogen or alkyl, and $R_2$ represents hydrogen, or $NH_2$ when $R_1$ represents $NH_2$, said diphenylamine and polyhydroxybenzene being present in an amount such that the ratio of the total number of moles of diphenylamine to the number of moles of polyhydroxybenzene is between 2 and 7.

16 Claims, No Drawings

DYE COMPOSITION CONTAINING DIPHENYLAMINE AND POLYHYDROXYBENZENE

The present invention relates to a dye composition for coloring keratinic fibers and in particular for the dyeing of living human hair, said composition comprising an admixture of one or more diphenylamines and a polyhydroxybenzene substituted or not, as a reducing agent.

The use of certain polyhydroxybenzenes for dyeing hair has been reported, for instance, in French Pat. Nos. 826,046; 1,537,199; 2,258,167; and 75 05 504 and British Pat. No. 1,063,979. However, these compounds are always employed as dyes, particularly in oxidation dye compositions and in oxidation dyeing procedures.

Further, certain polyhydroxybenzenes are also known for their antioxidant properties and principally for their use in the air stabilization of fats and oils, as described, for instance, in U.S. Pat. Nos. 2,763,691; 2,759,828; and 2,848,345.

Additionally, diphenylamines, such as the leucoderivatives of indophenols, indamines and indoanilines, are known for their use either alone, or in admixture with other dyes in hair dye compositions.

The color development for such compositions is generally effected either by the oxygen in the air, or by use of an oxidizing agent such as $H_2O_2$, urea peroxide or sodium persulfate.

One of the problems generally experienced in the field of dye compositions which are based on diphenylamines, results from the very nature of these compounds, i.e. they exhibit a tendency to oxidize. Often premature oxidation is experienced, especially with regard to the most oxidizable diphenylamines, either during their production, or during various stages of their use, or even during storage. The diphenylamines are transformed by oxidation into corresponding indophenols, indamines or indoanilines. In the present specification, the term "indoamines" includes the indophenols, indamines and indoanilines corresponding to the said diphenylamines. These compounds are generally unstable in an aqueous medium and thus exhibit reduced dyeing power.

Until now efforts to retard oxidation consisted essentially of using reducing agents conventionally employed in oxidation dyeing procedures and compositions such as sodium bisulfite or ascorbic acid as is known, for instance, from French Pat. No. 1,338,063.

Because of their oxidation-reduction protential, these conventional reducing agents must be employed in an amount such that they inhibit air oxidation of the diphenylamines during application of the dye compositions on the hair. This, in turn, results in a variation in the time required for the coloration of the hair.

The problem of premature oxidation and oxidation inhibition during the application of the dye composition to hair is more particularly experienced when diphenylamines or leucoderivatives of indophenols, indamines and indoanilines present in the composition are very oxidizable. In effect, oxidation by the oxygen of the air, if it provides several advantages in the dyeing of hair by reason of the fact that it avoids the necessity of producing mixtures at the moment of use and avoids the use of oxidation agents capable of reacting with the hair so as to sensitize it, also implies that the diphenylamines employed are easily oxidized and that they have a sufficiently low potential so that the oxygen of the air suffices as an oxidizing agent. On the other hand, the oxidation kinetics of these diphenylamines must be sufficiently rapid, so that color development is sufficiently rapid so as to avoid over a period of time variations in the colors achieved.

It has been noted that this problem is experienced generally for all diphenylamines, whose corresponding indoamines have an oxidation-reduction potential between $-450$ and $-350$ mv.

The objective then was to find a way to control the oxidation of these diphenylamines so as to prevent their premature oxidation during the production of dye compositions containing the same without, however, impairing their subsequent air oxidation when the dye composition is applied to the hair to be colored which is necessary to develop coloration on the hair.

It has now been found that this objective can be achieved by employing in hair dye compositions a combination of (a) diphenylamines or their salts, whose corresponding indoamines have an oxidation-reduction potential between $-450$ and $-350$ mv with (b) a polyhydroxybenzene or its salt, having an oxidation-reduction potential between $-600$ and $-300$ mv and having the formula

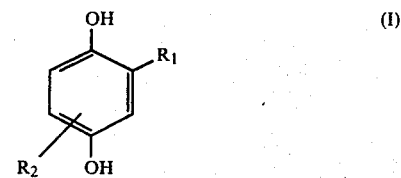

(I)

wherein $R_1$ represents hydroxy or

wherein $R_3$ represents hydrogen or alkyl, and $R_2$ represents hydrogen, or $NH_2$ when $R_1$ represents $NH_2$, the said diphenylamine and polyhydroxybenzene being present in an amount such that the ratio of the total number of moles of diphenylamine to the number of moles of said polyhydroxybenzene of formula (I) is between 2 and 7. The combination of these components provides a dye composition which does not oxidize prematurely during its production. Further, the dyeing of the hair is carried out rapidly with free air and the color achieved remains stable.

In the above formula for the polyhydroxybenzene, the alkyl group represented by $R_3$ designates more particularly a branched or linear lower alkyl having preferably 1 to 6 carbon atoms. Representative preferred alkyl groups include methyl, ethyl or propyl. Representative salts of the polyhydroxybenzene include the hydrochloride, hydrobromide or the sulfate thereof.

The oxidation-reduction potentials of the indophenols, indamines or indoanilines corresponding to the diphenylamines have been measured at a pH of 10 in a 25% ethanol solution in water ($HCO_3^-/CO_3^-$) whereas the oxidation-reduction potentials of the polyhydroxybenzenes have been measured at a pH of 10 in water ($HCO_3^-/CO_3^{--}$). The values are given in mv/SCE.

Representative particularly preferred polyhydroxybenzenes for use in the present invention include 1,2,4-trihydroxy benzene, amino hydroquinone, N-methylamino hydroquinone, 2,5-diamino hydroquinone, 2,6-diamino hydroquinone and 2,3-diamino hydroquinone.

It is indeed to be understood that in order for these polyhydroxybenzenes to function as a reducing agent, their oxidation-reduction potential must be such as to permit reduction of the indophenols, indamines and indoanilines formed in small amounts from the diphenylamines, during the preparation of the compositions, or during subsequent operations involving the use thereof or even during storage. These polyhydroxybenzenes exhibit oxidation-reduction kinetics which are sufficiently rapid so that they do not hinder color development during the application of the composition to the hair, when they are employed in the above indicated amounts.

The diphenylamines usefully employed in the compositions of the present invention whose corresponding indoamines have an oxidation reduction potential between −450 and −350 mv are essentially diphenylamines or leuco-derivatives of indoanilines, indophenols and indamines, which rapidly oxidize in air. The combination of the said polyhydroxybenzene in the amounts indicated above with these diphenylamines provides essentially two principal advantages:

(1) a reduction of the indoanilines, indophenols and indamines which are formed generally during the use of the diphenylamines is effected in an extremely rapid fashion thereby providing precise shades; and (2) the dyeing of the hair is rapidly effected in free air and the color thus achieved does not evolve in the days following the application of the composition.

The present invention also includes a composition containing a mixture of the diphenylamines possessing the oxidation-reduction potential values mentioned above and one or more diphenylamines which are less oxidizable and which generally require the addition of an oxidizing agent conventionally employed in capillary cosmetic formulations before the application of the same to the hair. In this embodiment, a rapid reduction of the indoanilines, indophenols and indamines to the corresponding leucoderivatives during the production of the composition is also effected, which also contributes to imparting a precise shade to the dye composition.

Moreover, the polyhydroxybenzene employed in the composition of the present invention is so selected that it does not impart its own color to the resulting composition so as not to interfere with the color resulting from the oxidation of the diphenylamines during the application of the latter to the hair.

Representative diphenylamines which are especially employed in the composition of the present invention include those having the formula

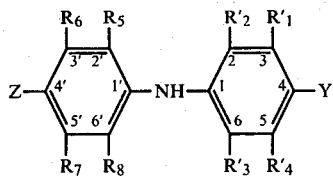

wherein $R_1'$ and $R_4'$ each independently represent hydrogen; a halogen such as chlorine or bromine; lower alkyl having 1–4 carbon atoms and preferably methyl and ethyl; lower alkoxy, such as, preferably, methoxy and ethoxy; acylamino having preferably 2–5 carbon atoms, such as, preferably, acetylamino; and ureido;

$R_2'$ and $R_3'$ each independently represent hydrogen; a halogen such as chlorine or bromine; lower alkyl; lower alkoxy; amino; amino, mono- or di-substituted by alkyl; N-carbalkoxy amino; N-hydroxy alkyl amino; acylamino; N-carbamyl alkylamino; or ureido, wherein the alkyl groups have, preferably, 1–4 carbon atoms and designate more particularly methyl or ethyl, the alkoxy groups have, preferably, 1–4 carbon atoms and represent particularly methoxy or ethoxy and, the acyl group has, preferably, 2–5 carbon atoms and represents, particularly, acetyl;

$R_5$, $R_6$, $R_7$ and $R_8$ each independently represent hydrogen; a halogen such as chlorine or bromine; lower alkyl having, preferably, 1–4 carbon atoms and representing, in particular, methyl or ethyl; and alkoxy having, preferably, 1–4 carbon atoms and in particular methoxy or ethoxy;

Y represents hydroxy or amino; and

Z represents hydroxy or

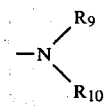

wherein $R_9$ and $R_{10}$ each independently represent hydrogen, lower alkyl, hydroxy alkyl, carbamylalkyl, aminoalkyl, mono- or dialkylaminoalkyl, acylaminoalkyl, alkylsulfonamidoalkyl, arylsulfonamidoalkyl, sulfoalkyl, piperidinoalkyl or morpholinoalkyl; as well as the salts of said diphenylamines, such as the hydrochloride, hydrobromide and sulfate thereof; and wherein the alkyl groups represent, preferably, those having 1–4 carbon atoms and more particularly methyl, ethyl and propyl, the acyl groups represent, preferably, those having 2–5 carbon atoms and more particularly acetyl and the aryl group represents, preferably, phenyl.

The present invention also relates to a process for protecting against premature or untimely oxidation of diphenylamines whose corresponding indoamines have a oxidation-reduction potential of −450 to −350 mv, said process comprising introducing into a solution containing said diphenylamines a polyhydroxybenzene as defined above having said oxidation-reduction protential values in an amount as also defined above.

Quite remarkable control of oxidation during the production of the composition and an absence of oxidation inhibition during the application of the composition to the hair are particularly achieved, in accordance with one preferred embodiment of the invention when as the polyhydroxybenzene there is selected trihydroxybenzene, N-methylamino hydroquinone, 2,5-diamino hydroquinone, 2,6-diamino hydroquinone for use in combination with the diphenylamine whose corresponding indoamine has an oxidation-reduction potential between −450 and −400 mv.

These hair dye compositions can also contain direct dyes, and particularly azo, anthraquinone and nitrobenzene dyes and amino quinone derivatives.

The compositions of the present invention are employed in the form of an aqueous solution which can contain alcohols such as, preferably, ethanol and isopropanol, as well as other solvents such as, preferably, glycols, for instance methyl glycol, ethyl glycol, butyl glycol, propylene glycol and the monomethyl ether of diethylene glycol. The said solvents are present in amounts between 0.5 and 40 percent and preferably 1 to 15 percent by weight of said composition.

The hair dye compositions according to the present invention can also include various components conventionally employed in cosmetic formulations such as wetting agents, for example, oxyethylenated alkyl phenols, oxyethylenated fatty acids, oxyethylenated fatty alcohols, sulfates and sulfonates of fatty alcohols optionally oxyethylenated, ethanolamines of fatty acids, dispersing agents, swelling agents, penetrating agents, emollients, polymers such as the polymers or copolymers of vinylpyrrolidone, thickening agents such as cellulosic derivatives as carboxymethyl cellulose, hydroxypropylmethyl cellulose, quaternary derivatives such as trimethyl cetylammonium bromide, perfumes, complexing agents such as ethylene diamine tetraacetic acid, alkalizing agents such as mono- or tri-ethanolamine, and acidifying agents such as phosphoric acid, lactic acid, acetic acid or citric acid.

The hair dye compositions of the present invention can be provided in the form of a gel, a foaming liquid, milky liquids of various viscosities packaged in hermetically sealed containers, in tubes or in an aerosol container.

One of the preferred embodiments of the present invention is the provision of the composition in the form of a foam, so as to improve the contact surface thereof with air when the composition is applied to the hair.

These foams can be provided in a conventional aerosol container together with a propellant. There can be employed a gaseous propellant such as nitrogen, nitrous oxide, a volatile hydrocarbon such as butane, isobutane or propane, or preferably fluorinated hydrocarbons sold under the name of Freon and belonging particularly to the class of fluorochlorohydrocarbons such as dichlorodifluoromethane (Freon 12), dichlorotetrafluoromethane (Freon 114), trichloromonofluoromethane (Freon 11). These propellants can be used alone or in any convenient combination. There is employed in a particularly preferred embodiment of the invention a mixture of Freons 114 and 12 in proportions ranging, respectively from 40:60 to 70:30.

The concentration of the diphenylamines used in the present invention is preferably between 0.01 to 5 percent by weight of the total composition and more preferably between 0.02 and 1 percent by weight of the total composition.

The pH of the composition of the present invention ranges between 5 and 11 and preferably between 8 and 9.5.

The hair dye composition of the present invention can be applied to the hair, before or after a shampooing, under the various forms described above and preferably under the form of an aerosol foam whereby the contact surface of the composition with the oxygen of the air is thus very significant.

The time of contact can vary from 2 to 40 minutes and is preferably between 5 and 30 minutes.

The following non-limiting examples are given to illustrate the invention.

Various supports or carriers, usefully employed in the present invention, include the following:

| Support A: thick milk | $A_1$ | $A_2$ |
|---|---|---|
| Sodium cetyl stearyl sulfate | 2 g | 2 g |
| Nonyl phenol oxyethylenated with 9 moles of ethylene oxide sold under the name of "Remcopal 349" | 5 g | 5 g |
| Hydroxy propyl methyl cellulose | 0.3 g | 0.3 g |
| Ethyl glycol | 10 g | 8 g |
| Support B: gel | | |
| Nonyl phenol oxyethylenated with 4 moles of ethylene oxide, sold under the name "Remcopal 334" | 7.5 g | |
| Nonyl phenol oxyethylenated with 9 moles of ethylene oxide, sold under the name "Remcopal 349" | 6 g | |
| Oleic acid | 1.5 g | |
| Copra diethanolamide | 3.5 g | |
| Ethyl alcohol - 96° titer | 4 g | |
| Propylene glycol | 1 g | |
| Butyl glycol | 2.5 g | |
| Support C: foaming liquid | $C_1$ | $C_2$ |
| Hydroxy propyl methyl cellulose | 0.5 g | 0.5 g |
| Sodium lauryl sulfate oxyethylenated with 2 moles of ethylene oxide (sold under the name Calve Delft 8533 - 30% active material | 5 g | 8 g |
| Copra diethanolamide | 5 g | 5 g |
| Butyl glycol | 8 g | 8 g |
| Support D | | |
| Sodium cetyl stearyl sulfate | 2 g | |
| Nonyl phenol oxyethylenated with 9 moles of ethylene oxide, sold under the name "Remcopal 349" | 5 g | |
| Ethyl glycol | 8 g | |
| Trimethyl cetyl ammonium bromide | 1.5 g | |
| Support E | | |
| Sodium lauryl sulfate oxyethylenated with 2 moles of ethylene oxide (sold under the name Calve Delft 8533 - 30% active material | 20 g | |
| Copra diethanolamide | 5 g | |
| Hydroxy propyl methyl cellulose | 0.3 g | |
| Butyl glycol | 5 g | |

Supports D and E, after introduction of the diphenylamine dyes and the polyhydroxybenzene reducing agent therein, are placed in an aerosol container by admixing, for example, 90 g of the total composition with, for example 10 g of a Freon 114/12 (40/60) mixture. This procedure provides an aerosol milk when support D is employed and an aerosol foam when support E is used.

The hair dye composition of the present invention is prepared by introducing the diphenylamine dyes and the polyhydroxybenzene reducing agent in any one of the supports mentioned above or any other conventionally employed carrier or support. The mixture is adjusted to a pH preferably between 5 and 11 by the incorporation therein of acid or a base, such as monoethanolamine or triethanolamine, for example, and the composition is completed by the addition of water in an amount sufficient to achieve 100 g of product.

Table I below illustrates representative compositions in accordance with the present invention. This Table indicates the amounts of diphenylamine dye, the amount of polyhydroxybenzene reducing agent, the nature of the support such as defined above, and the pH of the resulting composition, it being understood that water is added in the various examples in an amount sufficient to produce 100 g of said composition in each instance.

The compositions reported in Table I are applied to moist hair previously shampooed or not in amounts between 10 and 50 g as indicated in Table II below. These compositions are generally packaged in hermetically sealed filled containers or in aerosol containers when Supports D and E are employed.

The said compositions are permitted to remain in contact with the hair for a period of time ranging between 5 and 30 minutes, at a temperature varying between ambient temperature to 35° C. The color achieved is verified after rinsing the hair. The various operating conditions as well as the results of the dyeing operations are reported in Table II.

The oxidation-reduction potentials for the diphenylamines and polyhydroxybenzenes employed have been measured as indicated above. The oxidation-reduction potentials indicated for the diphenylamines correspond to the oxidation-reduction potentials of their corresponding indoamines.

TABLE I

| Compositions | Compounds | Concentrations g % | mole % $\times 10^{-3}$ | $\Sigma$Moles of leuco-derivatives $\times 10^{-3}$ | $\dfrac{\Sigma\text{Moles of leuco-derivatives} \times 10^{-3}}{\text{moles of reducing agent}}$ | Support | pH |
|---|---|---|---|---|---|---|---|
| 1 | 2-N-hydroxy ethylamino-4,4'-dihydroxy-5-methyl diphenylamine ($-434$ mv) | 0.5 | 1.8 | 1.8 | 2.25 | $A_1$ | 9 |
|  | 1,2,4-trihydroxy-benzene ($-410$ mv) | 0.1 | 0.8 |  |  |  |  |
| 2 | 2-amino-4,4'-dihydroxy-5-methyl diphenylamine ($-406$ mv) | 0.5 | 2.18 |  |  |  |  |
|  | 2,4'-diamino-4-hydroxy-5-methyl diphenylamine ($-388$ mv) | 0.2 | 0.87 | 3.05 | 6.78 | B | 9.5 |
|  | 2-N-methyl amino hydroquinone hydrobromide ($-400$ mv) | 0.1 | 0.45 |  |  |  |  |
| 3 | 2-carbamyl mehthyl amino-2',5-dimethyl-4-hydroxy-4'-N-ethyl, N-($\beta$-mesyl amino ethyl) amino diphenylamine ($-402$ mv) | 0.3 | 0.67 | 1.45 | 4 | $A_2$ | 9 |
|  | 2',3,5,5'-tetramethyl-4-hydroxy-4'-amino-diphenylamine ($-304$ mv) | 0.2 | 0.78 |  |  |  |  |
|  | 2-N-methyl amino hydroquinone hydrobromide | 0.08 | 0.36 |  |  |  |  |
| 4 | 2-amino-4-hydroxy-4'-N-methylamino-5-methyl diphenylamine ($-390$ mv) | 0.12 | 0.49 |  |  |  |  |
|  | 2-amino-2'-methyoxy-3,5-dimethyl-4-hydroxy-4'-N,N-dimethyl-amino diphenylamine ($-416$ mv) | 0.06 | 0.19 | 0.76 | 2.4 | $C_1$ | 9 |
|  | 3,5-dimethyl-4,4'-dihydroxy diphenylamine ($-321$ mv) | 0.02 | 0.08 |  |  |  |  |
|  | 1,2,4-trihydroxy benzene | 0.04 | 0.32 |  |  |  |  |
| 5 | 3,3',5,5'-tetramethyl 4-hydroxy-4'-amino diphenylamine ($-293$ mv) | 0.2 | 0.78 |  |  |  |  |
|  | 2-amino-2'-chloro-4,4'-dihydroxy-5-methyl diphenylamine ($-393$ mv) | 0.06 | 0.17 | 0.95 | 2.4 | D | 9 |
|  | 1,2,4-trihydroxy benzene | 0.05 | 0.4 |  |  |  |  |
| 6 | 2-amino-4-hydroxy-4'-N,N-(di-$\beta$-hydroxyethyl) amino-5-methyl diphenylamine ($-384$ mv) | 0.2 | 0.52 |  |  |  |  |
|  | 2,4'-diamino-4-hydroxy-5-methyl diphenylamine ($-388$ mv) | 0.1 | 0.44 |  |  |  |  |
|  | 2-amino-4,4'-dihydroxy-5-methyl diphenylamine | 0.6 | 2.60 | 3.56 | 2.8 | E | 9.5 |
|  | 1,2,4-trihydroxy benzene | 0.16 | 1.27 |  |  |  |  |
| 7 | 2,4'-diamino-4-hydroxy-5-methyl diphenylamine ($-388$ mv) | 0.3 | 1.3 |  |  |  |  |
|  | 3,5-dimethyl-4,4'-dihydroxy diphenylamine | 0.6 | 2.6 | 3.9 | 4 | D | 8.5 |

TABLE I-continued

| Compositions | Compounds | Concentrations g % | mole % x10⁻³ | ΣMoles of leuco-derivatives x10⁻³ | ΣMoles of leuco-derivatives x10⁻³ / moles of reducing agent | Support | pH |
|---|---|---|---|---|---|---|---|
| | 2-amino-hydroquinone hydrobromide ($-335$ mv) | 0.2 | 0.97 | | | | |
| 8 | 2-amino-2'-chloro-4-4'-dihydroxy-5-methyl diphenylamine ($-393$ mv) | 0.4 | 1.7 | | | | |
| | 2'-chloro-3,5-dimethyl-4-hydroxy-4'-N-methyl-amino diphenylamine $-275$ mv) | 0.2 | 0.72 | 2.42 | 2.55 | $C_1$ | 9 |
| | 1,2,4-trihydroxy benzene | 0.12 | 0.95 | | | | |
| 9 | 3,5-dimethyl-4-hydroxy-4'-amino diphenylamine ($-300$ mv) | 0.2 | 0.88 | | | | |
| | 2-amino-4-hydroxy-4'-N,N-(di-$\beta$-hydroxy ethyl) amino-5-methyl diphenylamine ($-384$ mv) | 0.4 | 1.05 | 1.93 | 4.83 | E | 9.5 |
| | 2,3-diamino-2-hydro-quinone hydrobromide ($-360$ mv) | 0.12 | 0.40 | | | | |
| 10 | 3,5-dimethyl-4-hydroxy-4'-N,N-dimethylamino diphenylamine ($-275$ mv) | 0.1 | 0.39 | | | | |
| | 2-N-hydroxy ethylamino-4,4'-dihydroxy-5-methyl diphenylamine ($-434$ mv) | 0.1 | 0.365 | | | | |
| | 2,5-dimethyl-4-hydroxy-4'-amino diphenylamine ($-276$ mv) | 0.2 | 0.88 | 1.635 | 2.6 | D | 8.5 |
| | 1,2,4-trihydroxy benzene | 0.08 | 0.635 | | | | |
| 11 | 2-amino-4,4'-dihydroxy-5-methyl diphenylamine | 0.4 | 1.74 | | | | |
| | 2,4'-diamino-4-hydroxy-5-methyl diphenylamine ($-388$ mv) | 0.2 | 0.87 | | | | |
| | 2-amino-4-hydroxy-4'-N-methylamino-5-methyl diphenylamine ($-390$ mv) | 0.2 | 0.82 | 3.43 | 6.86 | E | 9.5 |
| | 2,5-diamino hydroquinone dihydrobromide ($-570$ mv) | 0.15 | 0.5 | | | | |
| 12 | 3,5-dimethyl-4,4'-dihydroxy diphenyl-amine | 0.04 | 0.175 | | | | |
| | 2-amino-4-hydroxy-4'-N,N-(di-$\beta$-hydroxy ethyl) amino-5-methyl diphenylamine ($-384$ mv) | 0.06 | 0.19 | 0.755 | 4.44 | D | 9 |
| | 2',3,5,5'-tetramethyl-4-hydroxy-4'-amino diphenylamine ($-304$ mv) | 0.10 | 0.39 | | | | |
| | 2,3-diamino hydro-quinone dihydrobromide | 0.05 | 0.17 | | | | |
| 13 | 2-N-hydroxy ethyl amino-4,4'-dihydroxy-5-methyl diphenylamine ($-434$ mv) | 0.3 | 1.1 | 1.75 | | | |
| | 2-N-hydroxy ethyl amino-2'-chloro-4,4'-dihydroxy-5-methyl diphenylamine ($-437$ mv) | 0.2 | 0.65 | | | | |
| | 2-N-hydroxy-ethyl methoxy paranitraniline | 0.02 | | | 3 | D | 8.5 |
| | 2-amino hydroquinone hydrobromide | 0.12 | 0.58 | | | | |
| 14 | 2'-chloro-3,5-dimethyl-4-hydroxy-4'-N-methyl amino diphenylamine ($-275$ mv) | 0.5 | 1.81 | | | | |
| | 2,4'-diamino-4-hydroxy-5-methyl diphenylamine ($-388$ mv) | 0.2 | 0.87 | 2.68 | 4.2 | B | 10 |
| | 2-N-methyl amino hydroquinone hydro-bromide | 0.14 | 0.64 | | | | |
| 15 | 2-amino-2'-chloro-4,4'-dihydroxy-5-methyl | | | | | | |

TABLE I-continued

| Compositions | Compounds | Concentrations g % | mole % x10⁻³ | ΣMoles of leuco-derivatives x10⁻³ | ΣMoles of leuco-derivatives x10⁻³ / moles of reducing agent | Support | pH |
|---|---|---|---|---|---|---|---|
| | diphenylamine (−393 mv) | 0.26 | 1 | | | | |
| | 2'-chloro-3,5-dimethyl-4-hydroxy-4'-amino diphenylamine (−265 mv) | 0.2 | 0.76 | | | D | 9 |
| | 3,5-dimethyl-4-hydroxy-4'-N,N-dimethylamino diphenylamine (−275 mv) | 0.05 | 0.19 | 1.95 | 4 | | |
| | (4-nitro-3-N-methyl-amino) phenyl carboxy-methylether | 0.05 | | | | | |
| | 2-amino hydroquinone hydrobromide | 0.1 | 0.49 | | | | |
| 16 | 2-N-hydroxy ethyl amino-3'-chloro-4,4'-dihydroxy-5-methyl diphenylamine (−433 mv) | 0.3 | 0.98 | | | | |
| | 2-carbamyl methyl amino-2'5-dimethyl-4-hydroxy-4'-N-ethyl, N-(β-mesyl amino ethyl) amino diphenylamine | 0.1 | 0.22 | 2.02 | 4.3 | D | 9.5 |
| | 3,3'5-trimethyl-4,4'-dihydroxy diphenylamine (−316 mv) | 0.2 | 0.82 | | | | |
| | 2,6-diamino hydroquinone dihydrochloride (−425 mv) | 0.10 | 0.47 | | | | |
| 17 | 2-N-hydroxy ethyl amino-4,4'-dihydroxy-5-methyl diphenylamine (−434 mv) | 0.5 | 1.83 | | | | |
| | 2,4'-diamino-4-hydroxy-5-methyl diphenylamine (−388 mv) | 0.3 | 1.31 | 3.14 | 6.8 | A₂ | 9 |
| | 2-amino ethyl amino anthraquinone | 0.1 | | | | | |
| | 2,5-diamino hydro-quinone dihydrobromide (−570 mv) | 0.14 | 0.46 | | | | |
| 18 | 2-carbamyl methyl amino-2',5-dimethyl-4-hydroxy-4'-N-ethyl, N-(β-mesyl amino ethyl) amino diphenyl-amine | 0.3 | 0.67 | | | | |
| | 2',3,5,5'-tetramethyl-4-hydroxy-4'-amino diphenylamine | 0.2 | 0.78 | 1.83 | 4.82 | C₂ | 9.5 |
| | 2-amino-2'-chloro-4,4'-dihydroxy-5-methyl diphenylamine | 0.1 | 0.38 | | | | |
| | 2,6-diamino hydro-quinone dihydrochloride | 0.08 | 0.38 | | | | |

TABLE II

| Compositions | | | Application | | |
|---|---|---|---|---|---|
| No. | Quantity | Hair Being Treated | point in time | duration (min.) | Color Achieved |
| 1 | 20 g | Hair dyed blond with 60% of white hair | after shampooing | 5 | Coppery blond shade |
| 2 | 50 g | Bleached hair | before shampooing | 5 | Pearly coppery light blond shade |
| 3 | 20 g | Natural hair with 80% white hair | after shampooing | 10 | Bluish gray shade |
| | | Hair dyed blond | after shampooing | 10 | Ashen shade |
| 4 | 30 g | Hair dyed blond with 80% white hair | after shampooing | 3 | Irridescent blond |
| 5 | 20 g | Hair dyed light blond with 70% of white hair | after shampooing | 5 | Ashen light blond shade |
| 6 | 30 g | Natural light chestnut hair | before shampooing | 15 | Very luminous coppery mahogany chestnut |
| 7 | 20 g | Dyed chestnut hair with warm glints | after shampooing | 10 | Very luminous, brightened and intensified toward mahogany |
| 8 | 30 g | Bleached hair | after shampooing | 5 | Pastel golden beige shade |

TABLE II-continued

| Compositions | | | Application | | |
|---|---|---|---|---|---|
| No. | Quantity | Hair Being Treated | point in time | duration (min.) | Color Achieved |
| 9 | 30 g | Natural 70% white hair | before shampooing | 10 | Pretty mauve gray shade |
| 10 | 20 g | Natural deep blond hair | after shampooing | 10 | Deep ash blond shade |
| 11 | 30 g | Natural chestnut hair | before shampooing | 20 | Violet mahogany chestnut |
| 12 | 20 g | Hair dyed blond | after shampooing | 5 | Ash blond shade |
| 13 | 20 g | Hair dyed golden blond | after shampooing | 5 | Brightened toward coppery gold with strengthened color on the yellow ends |
| | | Natural light chestnut hair | after shampooing | 15 | Very luminous golden light chestnut |
| 15 | 20 g | Bleached hair | after shampooing | 5 | Delicate beige shade |
| 17 | 30 g | Natural light chestnut hair with 50% white hair | after shampooing | 10 | Chestnut shade with coppery mahogany glints |
| 18 | 30 g | Natural 80% white hair | after shampooing | 10 | Bluish gray shade |

EXAMPLE 14

Composition No. 14 reported in Table I is packaged in gel form, in tubes or hermetically sealed full containers, and exhibits good preservation characteristics.

At the moment of use, 0.5 g of sodium persulfate is added to 100 g of this product. The resulting mixture having a pH of 8 is then applied to the hair which is clean and moist. The mixture which is permitted to remain in contact with the hair for 5 minutes produces on hair dyed a deep blond, a rapid shading of the hair color towards a pearly ashen glint.

EXAMPLE 16

The composition No. 16 reported in Table I is packaged, out of contact with air, in the form of an aerosol milk.

To 60 g of this formulation, 40 g of $H_2O_2$ (20 volumes) are added. The resulting mixture has a pH of 7.5 and is then applied to dry hair. The mixture is permitted to remain in contact with the hair for 15 minutes. After rinsing and shampooing the thus treated hair, the said mixture produces on hair dyed light blond, or on bleached hair, a pearly beige shade.

EXAMPLE 19

Composition No. 18 reported in Table I is rapidly packaged, out of contact with air, in the form of a foamable liquid.

At the moment of use, 0.3 g of potassium ferricyanide is added to 100 g of this product. The resulting mixture is then immediately applied to moist, clean hair, the said mixture having a pH of 5. The mixture is permitted to remain in contact with the hair for 5 minutes and produces on white hair dyed 80% blond, a deep ashen blond shade.

EXAMPLE 20

A composition, essentially the same as that of No. 18 reported in Table I except that the pH thereof is adjusted to 5 by the addition of citric acid, is employed in essentially the same manner as reported in Example 19 except that the pH after the addition of potassium ferricyanide thereto is 3.7.

On the same color and type hair and for the same contact time, an ash blond shade is achieved using this composition.

What is claimed is:

1. A hair dye composition comprising an aqueous solution of at least one diphenylamine having the formula

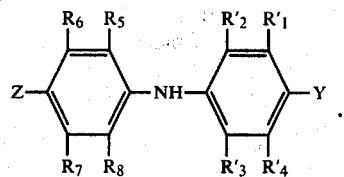

wherein
$R'_1$ and $R'_4$ each independently represent hydrogen, halogen, lower alkyl, lower alkoxy, acylamino or ureido;
$R'_2$ and $R'_3$ each independently represent hydrogen, halogen, lower alkyl, lower alkoxy, amino, amino mono- or di-substituted by lower alkyl, N-hydroxy alkylamino, acylamino, N-carbamylalkylamino, ureido or N-carbalkoxyamino;
$R_5$, $R_6$, $R_7$ and $R_8$ each independently represent hydrogen, halogen, lower alkyl or lower alkoxy;
Y represents hydroxy or amino; and
Z represents hydroxy or

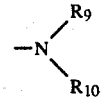

wherein $R_9$ and $R_{10}$ each independently represent hydrogen, lower alkyl, hydroxyalkyl, carbamylalkyl, aminoalkyl, mono- or di-alkylaminoalkyl, acylaminoalkyl, alkylsulfonamidoalkyl, arylsulfonamidoalkyl, sulfoalkyl, piperidinoalkyl or morpholinoalkyl, or a salt thereof; and a polyhydroxybenzene or a salt thereof, said diphenylamine being a leucoderivative of an indoamine having an oxidation-reduction potential between −450 and −350 mv measured at a pH of 10 in a 25% ethanol solution in water, said polyhydroxybenzene or the salt thereof having an oxidation-reduction potential between −600 and −300 mv measured at a pH of 10 in water, and said polyhydroxybenzene having the formula

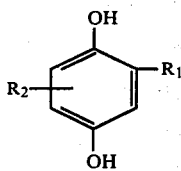

wherein
R₁ represents hydroxy or

wherein R₃ represents hydrogen or alkyl and
R₂ represents hydrogen, or NH₂ when R₁ represents NH₂; said diphenylamine being present in an amount sufficient to dye said keratinic fibers and said polyhydroxybenzene being present in an amount such that the ratio of the total moles of the diphenylamine to the number of moles of polyhydroxybenzene is between 2 and 7.

2. The composition of claim 1 wherein said polyhydroxybenzene is selected from 1,2,4-trihydroxybenzene, amino hydroquinone, N-methylamino hydroquinone, 2,5-diamino hydroquinone, 2,6-diamino hydroquinone and 2,3-diamino hydroquinone.

3. The composition of claim 1 wherein said polyhydroxybenzene is selected from the group consisting of 1,2,4-trihydroxybenzene, N-methylamino hydroquinone, 2,5-diamino hydroquinone, and 2,6-diamino hydroquinone and said diphenylamine is a leucoderivative of an indoamine having an oxidation-reduction potential between −450 and −400 mv measured at a pH of 10 in a 25% ethanol solution in water.

4. The composition of claim 1 wherein said diphenylamine is present in an amount between 0.01 and 5 percent by weight of the total composition.

5. The composition of claim 1 wherein said diphenylamine is present in an amount between 0.02 and 1 percent by weight of the total composition.

6. The composition of claim 1 having a pH between 5 and 11.

7. The composition of claim 1 having a pH between 8 and 9.5.

8. The composition of claim 1 which also includes a cosmetically acceptable organic solvent.

9. The composition of claim 8 wherein said organic solvent is an alcohol.

10. The composition of claim 8 wherein said organic solvent is present in an amount of 0.5 to 40 percent by weight of said composition.

11. The composition of claim 1 which also includes a surface active agent.

12. The composition of claim 1 which also includes a thickening agent.

13. The composition of claim 1 which also includes a cosmetic film-forming polymer.

14. The composition of claim 1 which also includes a perfume.

15. The composition of claim 1 packaged under pressure in an aerosol container and also containing an aerosol propellant.

16. A process for dyeing live human hair comprising applying to said hair an effective amount of the composition of claim 1 to dye said hair, permitting said composition to remain in contact with said hair for a period ranging from 2–40 minutes and thereafter rinsing said hair.

* * * * *